(12) United States Patent
Carter

(10) Patent No.: US 11,033,393 B2
(45) Date of Patent: Jun. 15, 2021

(54) HIP INTERPOSITIONAL SPACER

(71) Applicant: Accent Biomedical, Stow, MA (US)

(72) Inventor: Andrew J. Carter, Stow, MA (US)

(*) Notice: Subject to any disclaimer, the term of this patent is extended or adjusted under 35 U.S.C. 154(b) by 0 days.

(21) Appl. No.: 16/566,098

(22) Filed: Sep. 10, 2019

(65) Prior Publication Data

US 2020/0078178 A1 Mar. 12, 2020

Related U.S. Application Data

(60) Provisional application No. 62/729,151, filed on Sep. 10, 2018.

(51) Int. Cl.
*A61F 2/30* (2006.01)
*A61F 2/32* (2006.01)
*A61F 2/46* (2006.01)

(52) U.S. Cl.
CPC ............ *A61F 2/30756* (2013.01); *A61F 2/32* (2013.01); *A61F 2/4607* (2013.01); *A61F 2/4603* (2013.01); *A61F 2002/30026* (2013.01); *A61F 2002/30031* (2013.01); *A61F 2002/30069* (2013.01); *A61F 2002/30757* (2013.01)

(58) Field of Classification Search
CPC .......... A61F 2/30756; A61F 2/32; A61F 2/40; A61F 2/4607; A61F 2002/30757; A61F 2002/30026; A61F 2002/30031; A61F 2002/30327; A61F 2002/30574; A61F 2002/30934
See application file for complete search history.

(56) References Cited

U.S. PATENT DOCUMENTS

| | | | |
|---|---|---|---|
| 7,879,042 B2* | 2/2011 | Long | A61F 2/4607 606/99 |
| 2003/0114936 A1* | 6/2003 | Sherwood | A61F 2/30756 623/23.58 |
| 2013/0211529 A1* | 8/2013 | Frauens | A61F 2/30 623/18.11 |
| 2015/0282934 A1* | 10/2015 | Gray, Jr. | A61F 2/30756 424/423 |

* cited by examiner

*Primary Examiner* — Brian A Dukert
*Assistant Examiner* — Amanda M Barkan
(74) *Attorney, Agent, or Firm* — Pandiscio & Pandiscio

(57) ABSTRACT

A device and a method of treatment for osteoarthritis of a joint, such as the hip. The implant is an extensible cap that is placed over the femoral head.

17 Claims, 9 Drawing Sheets

HIP INTERPOSITIONAL SPACER

REFERENCE TO PENDING PRIOR PATENT APPLICATION

This patent application claims benefit of prior U.S. Provisional Patent Application Ser. No. 62/729,151, filed Sep. 10, 2018 by Accent Biomedical and Andrew J. Carter for HIP INTERPOSITIONAL SPACER, which patent application is hereby incorporated herein by reference.

FIELD OF THE INVENTION

This invention relates to surgical apparatus and methods in general, and more particularly to orthopedic surgical apparatus and methods.

BACKGROUND OF THE INVENTION

Osteoarthritis is one of the ten most disabling diseases in developed countries and worldwide affects approximately 10% of men and 18% of women aged older than 60 years. The World Health Organization estimates that aging populations and increasing life expectancy will make osteoarthritis the fourth leading cause of disability in 2020. Total hip arthroplasty (THA) can provide effective relief for patients with osteoarthritis of the hip where conservative treatment patterns have failed. Despite worldwide variations in cost, arthroplasty does appear to be cost effective in the long term.

Access to hip arthroplasty is more limited in the developing countries, and even in developed countries the procedure is less successful in younger patients.

There is a need for less expensive and less invasive solutions.

Partial resurfacing of the femoral head, or the use of prostheses that only treat the femoral head, have been used.

Osteochondral plugs, cylindrical implants that are placed into holes drilled through the articular surface into the underlying bone, have been investigated for use in a number of joints. While they have produced some success in terms of pain relief, there have been problems that have limited their appeal. A relatively common problem is the generation of cysts in the bone around the implant.

More particularly, the deficiency with this approach is that drilling into the underlying bone allows communication between the underlying bone and the synovial fluid within the joint. It is believed that the access of synovial fluid into the underlying bone leads to the development of cysts.

There is a need for a design of implant that does not require the underlying bone to be breached for the implant to be held in place.

Interpositional implants or spacers have been investigated for a number of joints such as the knee. Implants have been fabricated from polyurethanes and metals. Implants used in the knee have had mixed results, and while pain relief is generally achieved, issues have been seen that relate to inappropriate sizing of the device and the inability of the device to stay in place. Devices have also failed to be sufficiently robust to avoid wear and breakdown.

Surgeons have used tendons and fascia as an interpositional implant in a number of joints of the hand and foot. Tissue can either be autologous, i.e., taken from another part of the patient, or allogeneic, i.e., taken from another source. Artimplant, a Swedish company, has produced a range of synthetic implants from woven fibers of their resorbable ARTELON® polyurethane urea polymer for the CMC (carpometacarpal), STT (scaphoid-trapezium-trapezoid), MTP (Metatarsophalangeal), and DRU Spacer (distal radioulnar). Results obtained were mixed, and while pain relief was seen in many patients, a large number of patients needed to have re-operations to have devices removed. Review of the FDA's MAUDE database showed 147 adverse events related to the ARTELON® products. The level of complaints peaked in 2008 and 2009 with approximately 50 complaints each year. The majority of the adverse events resulted in explanation of the device, generally 6-24 months post implantation, for pain and swelling. Some cases appear to have been technique related, including trimming of the device resulting in loose fibers that caused inflammation, and poor fixation.

The ability to design an implant that can be easily implanted and held in place appears to be a significant problem, and no progress has been made in developing interpositional spacers for the hip. It appears that the issues of device design, materials of construction and surgical technique for introduction all need to be addressed and a novel solution identified.

SUMMARY OF THE INVENTION

The present invention comprises the provision and use of a novel elastomeric cap that is pulled or pushed over the femoral head, wherein the elastomeric cap has a smaller diameter collar that sits below the larger, maximum diameter of the femoral head when implanted. This provides a means for retaining the implant (i.e., the elastomeric cap) in place. The novel elastomeric cap generally comprises an outer surface which articulates against the acetabulum, an inner surface which seats on the head and neck of the femur, and a core which is disposed between the inner surface and the outer surface.

The device is designed to be resilient so as to act as a "shock absorber" to compensate for the lack of a patient's own articular cartilage in a joint afflicted with osteoarthritis.

The device also comprises surfaces made of high water-content materials which mimic articular cartilage in both water content and lubricity (providing a low friction surface). In addition, the surfaces of the device are resistant to tearing or wear. This is achieved by using polymeric hydrogels, specifically designed to have the desired qualities.

Furthermore, layers of polymeric hydrogels (i.e., polymer blends) are used so that the device has highly lubricious, highly hydrophilic, high water-content outer and inner surfaces, and a more hydrophobic, stronger core, disposed between the outer surface and the inner surface. More specifically, the layers comprise a blend of two polymeric hydrogels, wherein the first polymeric hydrogel has water content and elastic qualities and wherein the second polymeric hydrogel has strength and wear resistance qualities. The ratio of the two polymeric hydrogels are adjusted across the width of the device (i.e., across the thickness of the side wall of the novel elastomeric cap) such that the outer and inner surfaces comprise a greater portion of the first polymeric hydrogel and a lesser portion of the second polymeric hydrogel, and the center core comprises a greater portion of the second polymeric hydrogel and a lesser portion of the first polymeric hydrogel. In this way, the outer and inner surfaces of the device can be engineered to have ideal properties as low friction surfaces and the central core of the device can be engineered to provide strength. Importantly, the layers are indistinct from each other such that there is mixing of the layers at the each of the interfaces between the layers.

In one preferred form of the present invention, there is provided apparatus for treating osteoarthritis in a joint having a bone with a convex end, the apparatus comprising:
an elastomeric cap comprising:
a balloon-shaped region sized to fit over the convex end of the bone; and
a collar-shaped region extending from the balloon-shaped region, the collar-shaped region having a diameter that is smaller than the maximum diameter of the balloon-shaped region;
wherein the elastomeric cap is retained on the convex end of the bone by means of the collar-shaped region.

In another preferred form of the present invention, there is provided a method for treating osteoarthritis in a joint having a bone with a convex end, the method comprising:
providing apparatus for treating osteoarthritis, the apparatus comprising:
an elastomeric cap comprising:
a balloon-shaped region sized to fit over the convex end of the bone; and
a collar-shaped region extending from the balloon-shaped region, the collar-shaped region having a diameter that is smaller than the maximum diameter of the balloon-shaped region;
wherein the elastomeric cap is retained on the convex end of the bone by means of the collar-shaped region;
accessing the joint;
dislocating the joint;
fitting the elastomeric cap over the convex end of the bone; and
reducing the joint.

DETAILED DESCRIPTION OF THE PREFERRED EMBODIMENTS

A novel approach to treating osteoarthritic hips has been invented. The device and surgical approach require minimal surgical intervention and the procedure is likely usable in developing countries with limited facilities, and the simplicity of the implant suggests that this could be a cost-effective solution for these countries. Within the developed countries such as the USA, there is still a desire for fast and simple surgical techniques and inexpensive implants.

A further benefit of the device of the present invention is that "no bridges are burnt" and, if required, the implant can be simply removed, leaving the native anatomy untouched by surgery. Thus the new device of the current invention could be implanted and, subsequently, any other procedure (such as a total hip replacement) can still be done.

Figure 1:
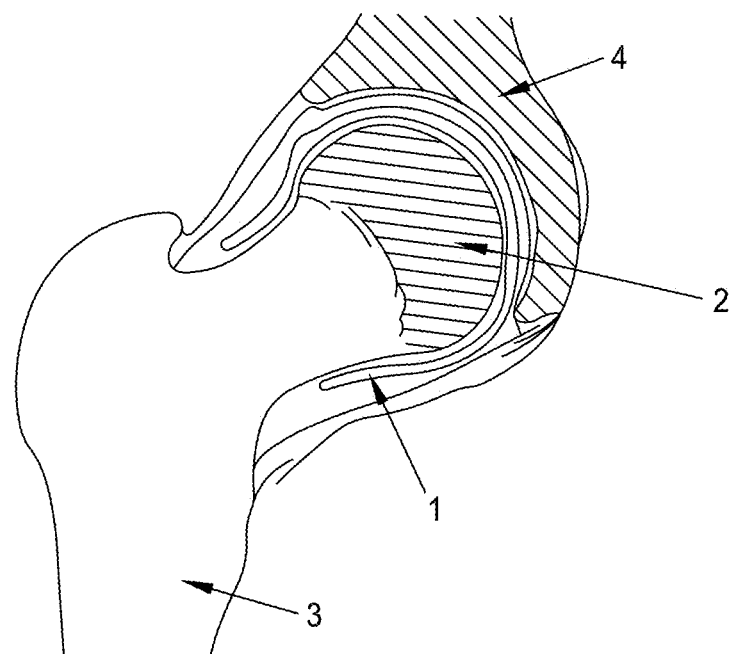
FIG. 1 shows a device 1 of the invention in place on the femoral head 2 of a femur 3 with the head placed into the acetabular cup 4.
Figure 2:
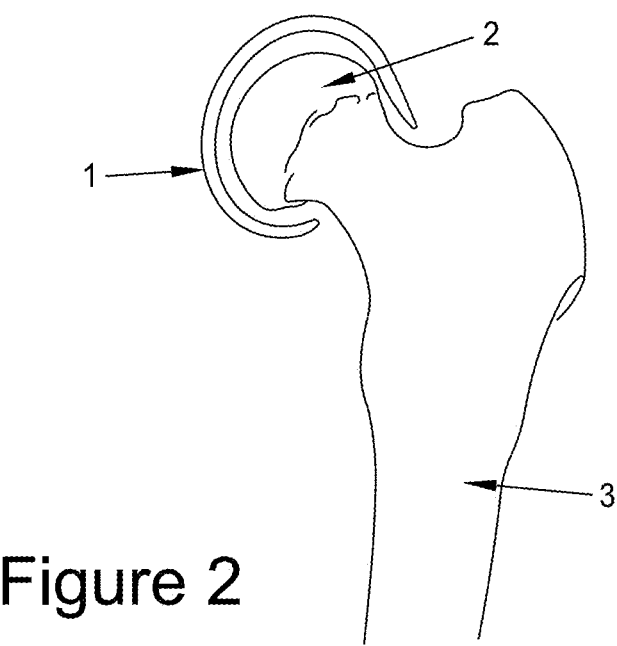
FIG. 2 shows a device 1 of the invention in place on the femoral head 2 of a femur 3.

The device is an elastomeric cap 1 that is pulled or pushed over the femoral head 2 as is shown in FIGS. 1 and 2. Access to the hip joint is gained using the conventional anterior or posterior approach of a hip arthroplasty. As with a hip arthroplasty, once access to the joint has been gained, the joint is dislocated. After placement of the novel elastomeric cap on the femoral head, the previously-dislocated joint is placed back in the acetabular cup and the surgical incision is closed.

Alternatively, access may be gained using the Ganz osteotomy, also known as "Peri-acetabular osteotomy" (PAO) or "the Bernese Osteotomy".

Figure 3:
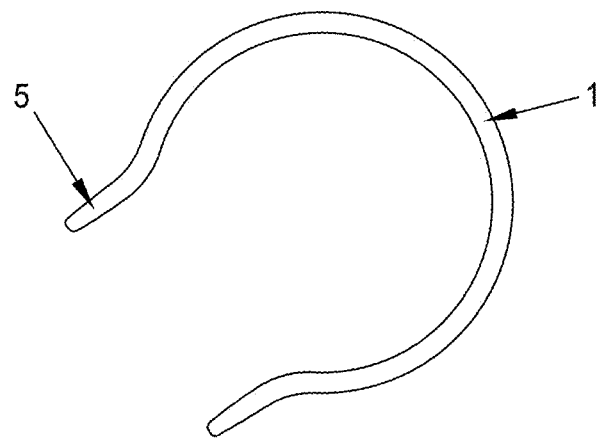
FIG. 3 shows a device 1 of the invention showing the reduced diameter region 5 that facilitates device retention during use.
Figure 4:
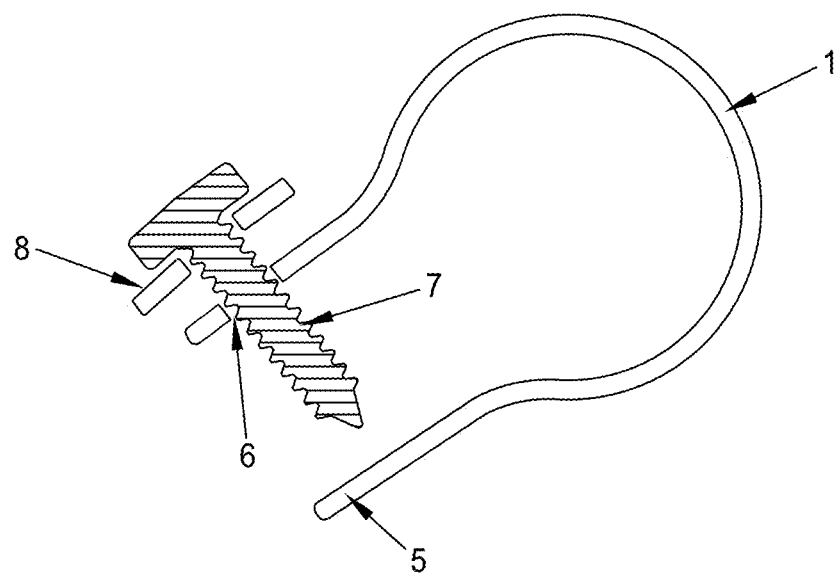
FIG. 4 shows a device 1 of the invention and showing the reduced diameter region 5 that is extended to facilitate device placement and retention. Also shown are optional holes 6 in the device to allow fixation of the device to the femur using a screw 7 and an optional washer 8.

As can be seen in FIG. 3, the cap 1 has a smaller diameter collar 5 that sits below the maximum diameter of the femoral head. This provides a means of retaining the implant in place. In some instances the collar(s) 5 may be extended, e.g., as shown in FIG. 4 where the extended collar 5 allows an introducing instrument (not shown) to hold the collar and, optionally, to apply lateral force to the implant to help facilitate implantation of the implant. The collar 5 may be trimmed post-implantation to reduce its length.

The device is designed to be resilient and so can act as a "shock absorber" to compensate for the lack of the body's own articular cartilage to provide that function. The surfaces of the device are also high water-content materials and, as such, they mimic articular cartilage in both water content and in lubricity and the ability to provide a low friction surface.

While it is not believed to be necessary, some surgeons may wish to apply additional fixation to further prevent the device from coming off the femur. To this end, the device 1, as shown in FIG. 4, may have a hole 6 or multiple holes to allow a screw or screws 7 to be driven into the femur to affix the cap. Optionally a washer 8, either plain or spiked, may be used.

To be successful, the device 1 needs to be able to provide a combination of lubricious surfaces with strength to resist damage. The material of the device needs to be lubricious and low friction but strong and resistant to tearing or wear. The outer surface 9A of the device 1 ideally needs to be a hydrogel to provide a lubricious surface to act against the patient's articular cartilage. As the water content and elasticity of polymeric hydrogels increase, the strength and wear resistance of the hydrogel reduces.

While it may be possible to find a single polymer that is capable of providing these properties, alternative, and perhaps simpler, methods of achieving the necessary properties of the device have been identified.

Polyurethane chemistry is very flexible and is capable of making biocompatible polymers capable of being safely implanted in the body. It is also possible, using polyurethane chemistry, to make hydrophilic (hydrogel) and hydrophobic polymers, and highly elastomeric low stiffness materials and high stiffness materials. The commonality of the components of the polyurethanes means that they possess a reasonable compatibility and may be mixed, or blended, together.

By producing an implant by the application of layers of a polymer blend, it is possible to engineer a material with highly lubricious, highly hydrophilic, high water-content outer and inner surfaces 9A and 9B, and gradually increase the proportion of a second, more hydrophobic, stronger polymer, such that the center of the device, i.e., the center or core 9C of the side wall, is a strong reinforcing polymer. In this way the outer and inner surfaces of the device can be engineered to have ideal properties as a low friction surface, and the strength requirement may be provided by a central core (i.e., the center of the side wall) of higher strength material. The central region of the side wall of the device (i.e., core 9C) does not need to be a hydrogel.

Figure 5:
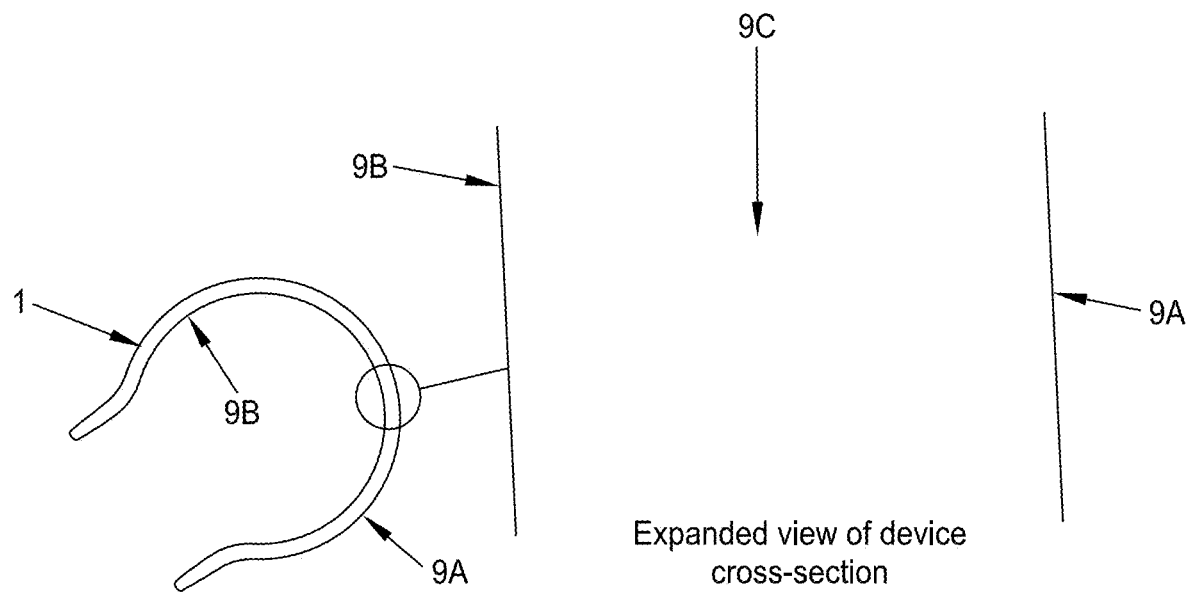
FIG. 5 shows a device 1 of the invention and showing an enlarged view of the cross-section of the device. The outer and inner surfaces 9A and 9B, respectively, of the device, and the core 9C, are also indicated. The graph in the figure shows the variation in the % of the second polymer incorporated in the device, showing that the proportion of polymer 2 (i.e., the second polymer) in the device is low at the outer and inner surfaces 9A and 9B of the device and the proportion of polymer 2 in the device is higher at the center of the device (at the core of the device).
Figure 5:
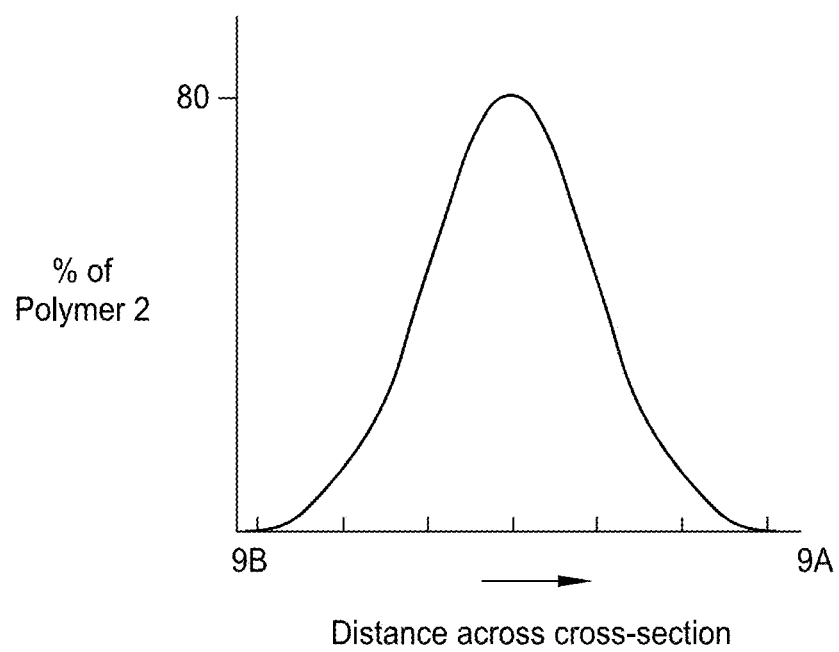

In FIG. 5 an enlarged view of the cross-section of the device shows the compositional variation between the outer and inner surfaces 9A and 9B and center of the side wall of the device (i.e., the core 9C of the device). The maximum percentage of the second polymer is provided for illustrative purposes only, and as one skilled in the art will know, a range of compositions may be used, depending on the stiffness required and the stiffness of the polymers being used.

Figure 6:
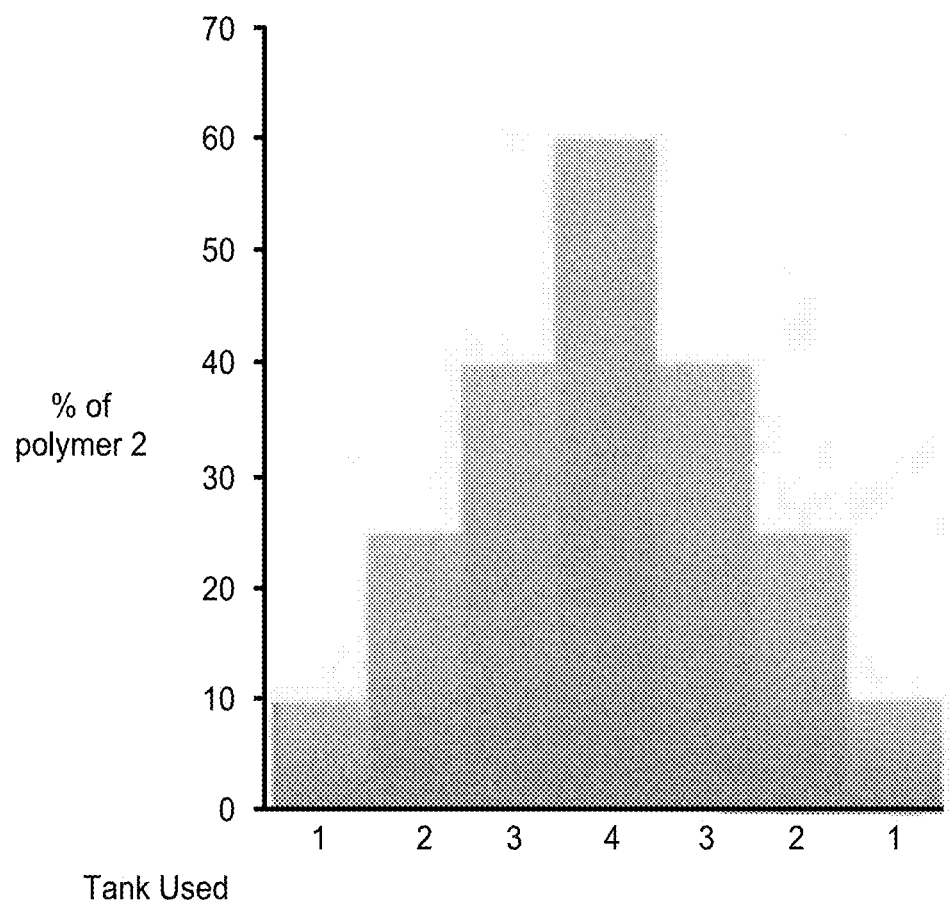
FIG. 6 shows the polymer blend formulation used in a device having seven different layers (where each layer has a different polymer formulation). These are indicated by the different tank numbers used to form the seven-layer device.

In FIG. 6 an illustrative example of the compositional variation of a device with seven layers is shown. Depending on the method of manufacture, the thickness of each layer may vary. Also, the overall thickness of a device may vary. It is possible that in the example shown in FIG. 6, the composition of each layer may be applied a number of times in order to allow a required overall thickness to be built up. The number of layers in the figure (i.e., seven) is shown as an example only, and in practice the number of layers may vary from three to nine or more.

Figure 7:
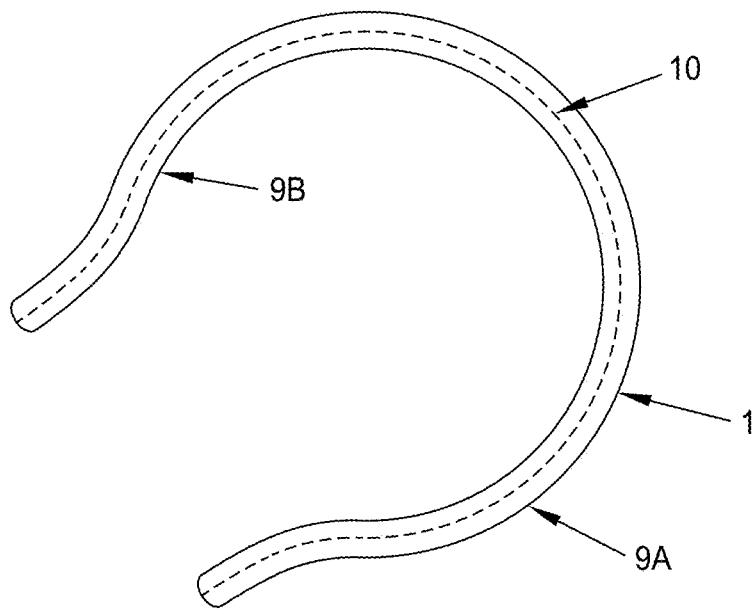
FIG. 7 shows a device 1 of the invention with a reinforcing layer 10 placed in the center of the device remote from the outer and inner surfaces 9A and 9B.

In FIG. 7 an alternative means of providing reinforcement to the device 1 is shown, wherein a reinforcing layer 10 is placed in the middle of the device 1 mid-way between the two surfaces 9A and 9B. The reinforcing layer 10 may be fabricated from a range of materials but is preferably a fabric.

Figure 8:
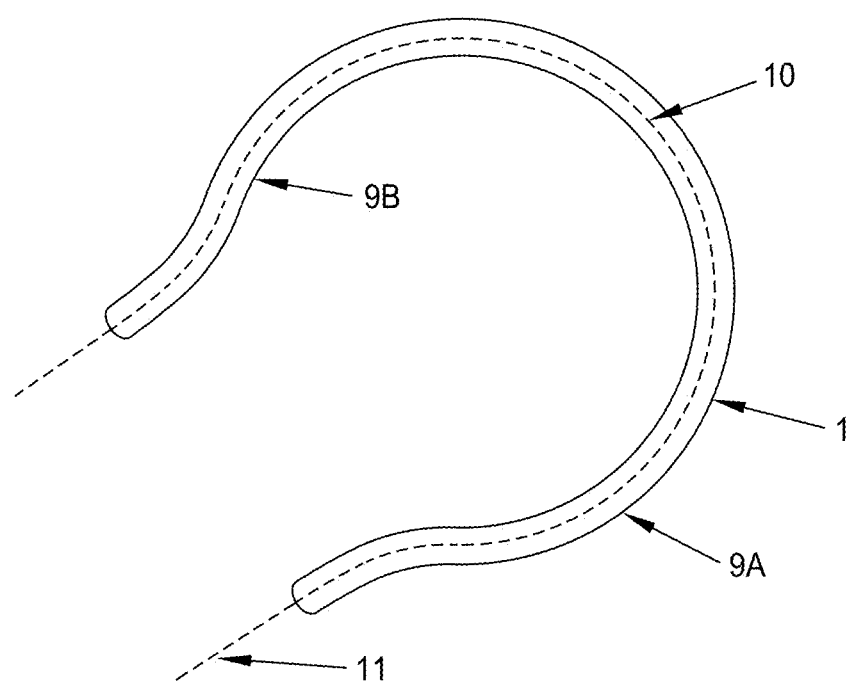
FIG. 8 shows a device 1 of the invention with a reinforcing layer 10 placed in the center of the device remote from the outer and inner surfaces 9A and 9B, wherein the reinforcing layer 10 is extended beyond the reduced diameter region.

The reinforcing layer 10 may extend beyond the collar of the device, e.g., as is shown in FIG. 8 where the extended portion 11 may be used to aid implantation of the device so as to allow the device to be gripped and pulled over the femoral head.

As a patient develops osteoarthritis, their joint space narrows as the articular cartilage wears and is lost. Surgeons monitor this joint space reduction and use it to determine an appropriate time for intervention. For the device of this invention, the opportunity exists to replace the space created by this lost material and so the thickness of the device can be configured to reconstitute the patient's original joint space. Thus devices of the invention may vary between 1 mm and 6 mm in thickness, or more frequently between 2 and 4 mm.

While manufacturing a device of the current invention does not require any specific polymer to be used, polyurethanes, and particularly aliphatic polyether polyurethanes, are particularly well suited. Suitable polymers include, for example, the Tecophilic™ aliphatic polyether polyurethanes manufactured by Lubrizol. For the high water content component, 70A or 83A shore hardness grades can be used, and the second reinforcing polymer can be a 41D shore hardness grade. Alternatively, a non-hydrophilic second polymer such as a Tecoflex™ aliphatic polyether polyurethane can be used. Other manufacturers of polyurethanes could similarly be used to source polymers suitable for the manufacture of devices of this invention.

Other hydrogel materials that can be used include polyacrylamides, polyacrylic acid-based polymers, and polysaccharides.

While it is preferable to use a hydrogel polymer for the present invention, it is not essential and suitable properties may be derived from non-hydrogel polymers, or polymers with a low water capacity, e.g., of 0.5-3%. One example of such materials is the Bionate polycarbonate polyurethanes manufactured by DSM.

While it is possible to produce the required variation in properties by using blends of just two polymers, the desired performance may be produced by using blends of more than two polymers. The additional polymers may act as compatibilizers to aid the blending of the polymers.

There are a number of manufacturing methods that can be employed to make a device of this invention. These methods include dip coating, spray coating or electrospinning. All techniques are used to form the device on a mandrel that has the desired device shape. Dip coating is an extremely efficient process and is used to manufacture condoms and gloves on a mandrel. Mandrels are dipped in polymer solutions sequentially. So, for the example in Example 6, there would be four tanks containing the different polymer blend formulations and the mandrel would be dipped in each one sequentially. If deemed necessary, a pause step between each dip operation would allow partial drying of the coating. Multiple dips in each tank would allow the coating thickness of a particular "layer" to be increased if desired. After the final coating the mandrel is placed in an oven to dry. The finished device is then removed from the mandrel.

The example described above has both device surfaces 9A and 9B having the same composition. This may not be desired in all cases and it is possible to make a device with a more lubricious surface on one surface 9A. Indeed, it may even be desired to have a non-lubricious surface 9B adjacent to the femoral head. These design variations may be simply achieved by appropriate selection of the coating formulations for each layer.

Figure 11:
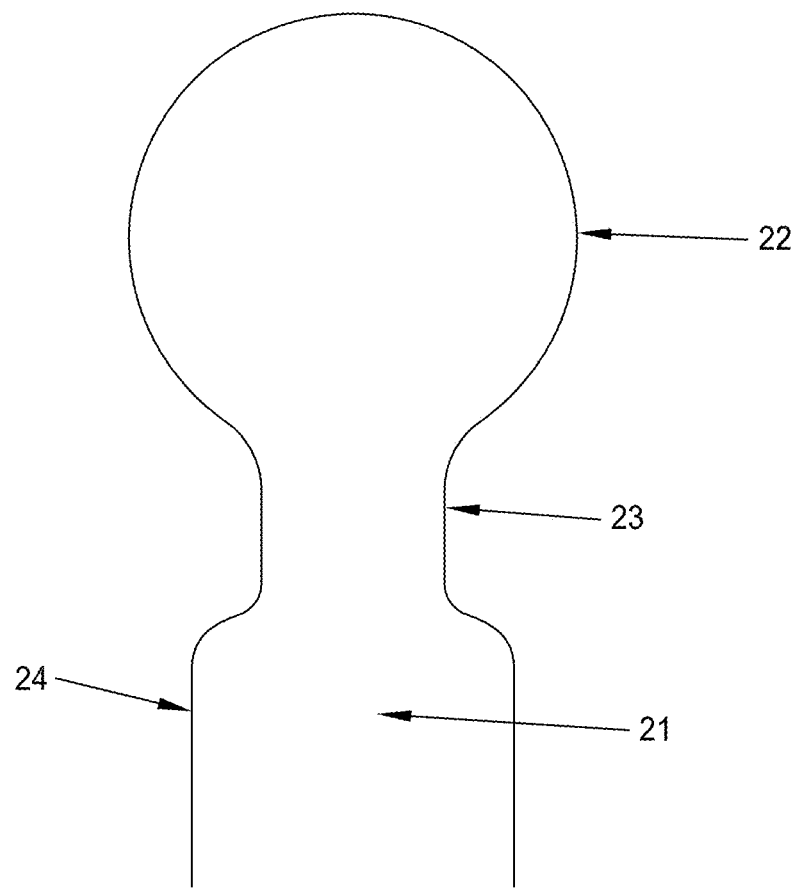
FIG. 11 shows a mandrel 21 suitable to be used as a former to manufacture a device of the invention. The mandrel has a larger diameter portion 22 to produce the femoral head region of the device and a reduced diameter collar region 23. The mandrel may also have an expanded diameter region 24 used to facilitate removal of the implant.

FIG. 11 shows, in cross-section, a mandrel that could be used to produce an implant 1 of the present invention. The spherical portion 22 represents the desired inner diameter of the implant and the reduced collar area is represented by the region 23. In some instances it may be desired to produce an implant longer than required by dipping down into the region 24 of the mandrel. This would provide an area that can be gripped, or rolled back, to facilitate removal of the implant from the mandrel. The mandrel may be fabricated from metal or ceramic and may be coated to facilitate the coating process.

For spray coating, a series of spray nozzles will spray the series of polymer blend solutions onto a mandrel. A turntable may optionally be used to rotate the mandrel. Subsequent to applying the polymer coatings, the device will be dried.

Where a reinforcing layer is to be added, this may be done after the first half of the device has been coated onto the mandrel.

For electrospinning, a similar set-up to that used for spray coating will be used. A voltage potential will be applied between the needle delivering the polymer solution and the mandrel.

A further refinement of the use of electrospinning is that a bicomponent, or sheath-core fiber structure, can be produced with a central reinforcing core and an outer hydrogel material.

Alternatively, two delivery needles can be used for the electrospinning, one delivering hydrogel and the other delivering the reinforcing polymer. By control of the flow rates during electrospinning, the proportion of each fiber may be varied throughout the device thickness to generate the desired properties for each layer of the device, e.g., a higher lubricity surface 9A and a strengthened core 9C.

For all the manufacturing methods there will not be, and is preferred not to be, a distinct boundary between subsequent (i.e., adjacent) layers, and the fact that there is still some solvent present will cause a mixing at the interface between adjacent layers. Distinct layers are an undesirable feature as they will provide points of weakness and can initiate failure. The manufacturing techniques identified all lend themselves to providing merged layers, i.e., layers without a distinct interface with the adjacent layer in the device.

Subsequent to the drying process of manufacture, devices can be removed from the mandrel. The elastomeric nature of the device allows this to be done easily.

It is also possible that devices of the invention could be produced by injection molding or by extrusion blow molding or by multi-layered extrudates.

Prior to use the device needs to be hydrated. This can be done prior to packaging and sterilization such that the device is supplied ready to use, or alternatively the device may be packaged dry and hydrated by the surgeon immediately prior to use.

Devices may be hydrated in water or saline. Optionally, other materials can be added to the hydrating solution, e.g., hyaluronic acid to further aid lubricity, analgesics to provide post-operative pain relief, antibiotics for infection prophylaxis, etc., or combinations thereof.

The use of a hydrogel allows the device to be used for drug delivery of any water soluble drug that may be simply loaded into the device post fabrication. Drug delivery may be for both short term treatment of post-operative pain or may be a longer term treatment.

For other drug delivery options, the drug formulation may be loaded into a specific layer of the device during fabrication.

While primarily designed for use in the hip, those skilled in the art will recognize that this invention may be applied to other joints in the human body such as the shoulder, fingers and toes.

A critical aspect of the invention is that the subchondral bone layer is not breached during placement of the device, or as a means of holding the implant in place.

Those skilled in the art would also recognize the suitability of this approach to provide a cost-effective means of treating animals.

Figure 9:
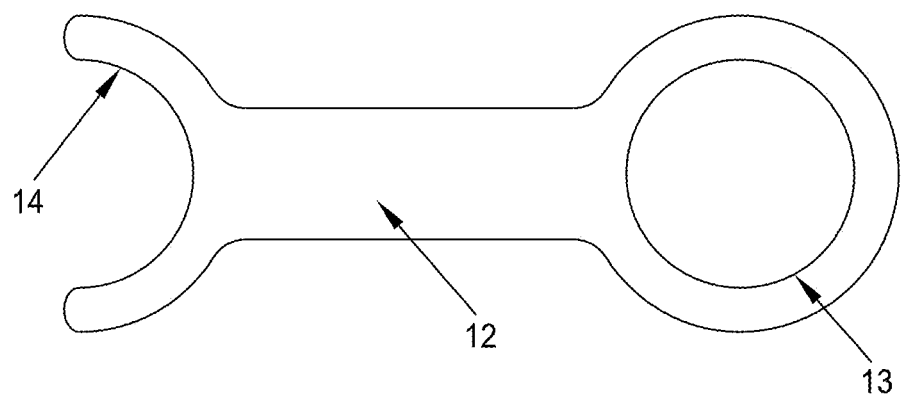
FIG. 9 shows a device 12 for intra-operative sizing of the femoral head. The opening 13 is placed over the femoral head. The open end of the device 14 may be used to measure the diameter of the femoral neck.

To aid the surgeon during surgery, simple gauges comprising circular holes may be used to determine the size of the implant required. An example of a suitable gauge is shown in FIG. 9 where the femoral head diameter can be assessed using the opening 13 and the diameter of the femoral neck can be measured using the open end 14. A series of gauges corresponding to the variety of diameters of implant available would be provided. It is preferred that the device is sized to provide a close fit to the femoral head diameter. Using an undersized implant that would remain stretched after implantation is not desired. The pressure resulting from an undersized implant could lead to damage to the remaining cartilage on the femoral head.

During surgery the surgeon may use a burr or other means to remove any osteophytes, and may trim any torn soft tissue. If the femoral head has become non-circular, a burr may also be used to trim the head to better fit a device, taking care not to breach the subchondral bone layer.

It is strongly preferred to not compromise the subchondral bone surface, and in this respect devices of the current invention differ from "osteochondral plug" designs wherein the anchoring of the device is provided by extending it into the subchondral bone space, either as a cylindrical plug or by use of anchoring pegs. The deficiency of this approach (i.e., the prior art "osteochondral plug" designs) is that it allows access of synovial fluid into the subchondral bone space, which is believed to lead to cyst formation. Designs of the current invention avoid this by being in the form of caps that sit over the subchondral bone.

In instances where the subchondral bone is breached, either in implant preparation, or through the progression of disease, the surface of the bone may be optionally sealed by application of a bone cement or bone void filler.

Figure 10:
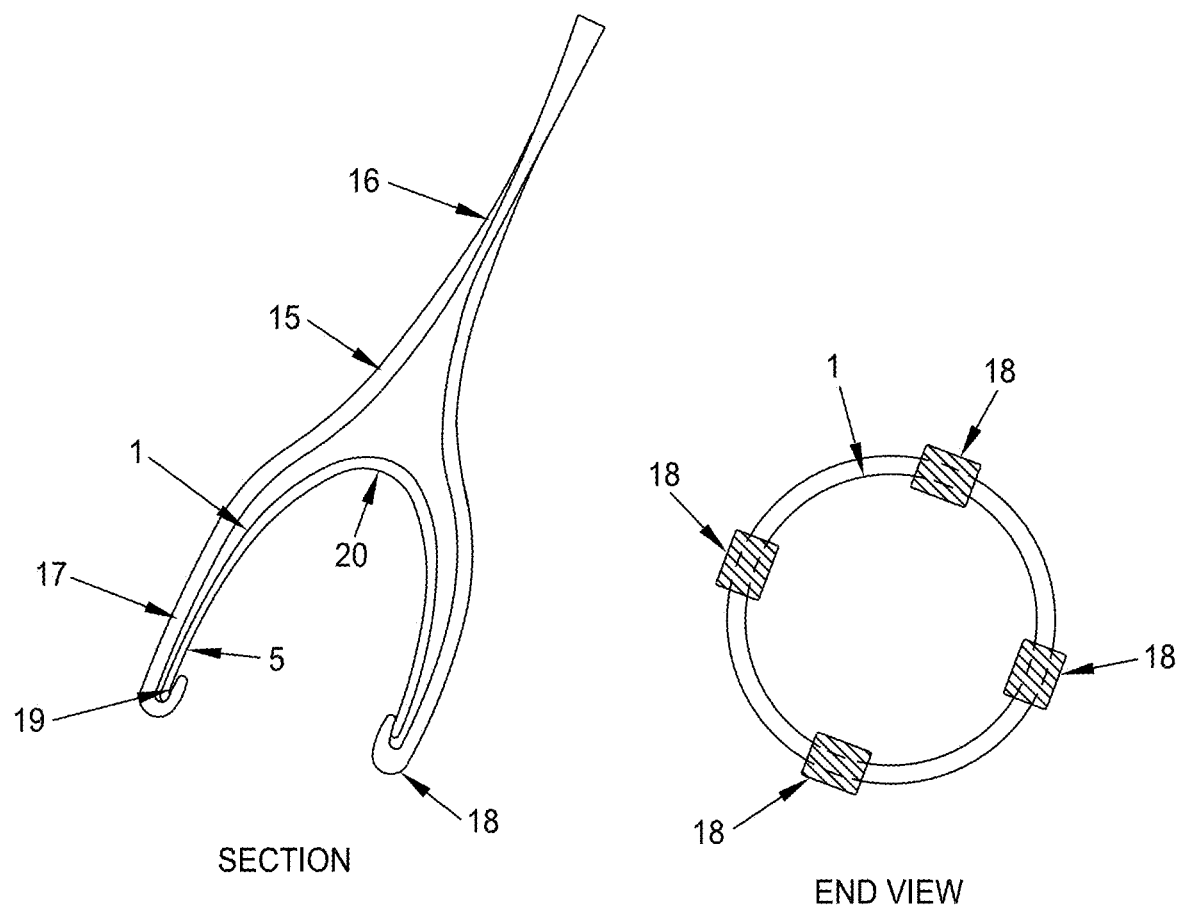
FIG. 10 shows an example of an insertion tool 15, with a handle 16, prongs or tines 17, also showing the rounded ends of the prongs or tines 18 and a clip section 19 that releasably retains the device 1.

While it would be possible to implant a device by pulling it "by hand" over the femoral head, it may be preferred to use a device to facilitate the implantation. An example of a device that could be used is shown in FIG. 10. The implantation device 15 has a handle 16 for the surgeon to hold. The implantation device has multiple tines, or prongs, 17. In the example shown there are four tine, or prongs, 17, but an implantation device could have more or less. The tines are compressed inwardly, either by hand or using a sleeve (not shown), to the approximate diameter of the collar region 5 of the implant 1. The implant 1 is placed in the device and the ends of the collar region of the device 5 are placed in the recesses 19 in the tines. The tines are then allowed to return to their relaxed position of FIG. 10, and in doing so the collar region of the device is stretched open to allow it to be pushed over the femoral head. Once the top of the implant 20 is seated on the femoral head, pushing the insertion device further distally serves to release the ends of the collar of the device from the recesses 19. The insertion device can then be removed, leaving the implant in place.

It should be appreciated that it is possible to implant the device over the femoral head in other ways. By way of example but not limitation, the device may be everted prior to implantation and then "rolled out" over the femoral head (and femoral neck), e.g., in a manner which is similar to the way in which a condom is applied. In this way, a surgeon can easily deploy the device over the femoral head (and femoral neck) without having to use any additional tool(s) to help facilitate implantation.

EXAMPLES

The following Examples are presented for illustrative purposes only, and do not limit the scope or content of the present application.

Example 1

A mandrel was produced from stainless steel to the design shown in FIG. 11 with a 30 mm diameter head. Blends of Tecophilic SP-80A-150 (80 Shore A hardness and 150% equilibrium water content) and Tecophilic SP-60D-60 (60 Shore D hardness and 60% equilibrium water content), supplied by Lubrizol, were made in 5 1 liter beakers with the following compositions:
  a. Tank 1—90% SP-80A-150: 10% SP-60D-60
  b. Tank 2—70% SP-80A-150: 30% SP-60D-60
  c. Tank 3—50% SP-80A-150: 50% SP-60D-60
  d. Tank 4—30% SP-80A-150: 70% SP-60D-60
  e. Tank 5—10% SP-80A-150: 90% SP-60D-60

The mandrel was slowly dipped into Tank 1 and removed. It was inverted to stop drip formation and left to dry for 1 minute. The mandrel was then dipped into Tank 2 and similarly removed and inverted. The sequential dipping continued through to Tank 5, after which the mandrel was dipped into Tank 4, Tank 3, Tank 2 and finally Tank 1. The coated mandrel was then placed in a vacuum oven to dry overnight with an air flow of 0.5 L/min. The implant could then be removed from the mandrel. The application of the coatings to incompletely dried prior coatings meant that there were no distinct boundaries between the layers.

Example 2

An implant from Example 1 was hydrated by placing it in phosphate-buffered saline. The resultant implant was flexible, had lubricious surfaces and could be applied over the mandrel to simulate placement over a femoral head.

Example 3

An implant from Example 1 was hydrated by placing it in an aqueous solution of hyaluronic acid. The resultant implant was flexible, had lubricious surfaces and could be applied over the mandrel to simulate placement over a femoral head.

Example 4

Blends of Tecophilic SP-80A-150 (80 Shore A hardness and 150% equilibrium water content) and Tecoflex EG-100A (100 Shore A hardness and ~0% equilibrium water content aliphatic polyether polyurethane), supplied by Lubrizol, were made in 5 1 liter beakers with the following compositions:
  a. Tank 1—90% SP-80A-150: 10% EG-100A
  b. Tank 2—70% SP-80A-150: 30% EG-100A
  c. Tank 3—50% SP-80A-150: 50% EG-100A
  d. Tank 4—30% SP-80A-150: 70% EG-100A
  e. Tank 5—10% SP-80A-150: 90% EG-100A The mandrel was slowly dipped into Tank 1 and removed. It was inverted to stop drip formation and left to dry for 1 minute. The mandrel was then dipped into Tank 2 and similarly removed and inverted. The sequential dipping continued through to Tank 5, after which the mandrel was dipped into Tank 4, Tank 3, Tank 2 and finally Tank 1. The coated mandrel was then placed in a vacuum oven to dry overnight with an air flow of 0.5 L/min. The implant could then be removed from the mandrel. The application of the coatings to incompletely dried prior coatings meant that there were no distinct boundaries between the layers.

Example 5

An implant from Example 4 was hydrated by placing it in phosphate-buffered saline. The resultant implant was flexible, had lubricious surfaces and could be applied over the mandrel to simulate placement over a femoral head.

Example 6

An implant from Example 4 was hydrated by placing it in an aqueous solution of hyaluronic acid and 3% lidocaine hydrochloride. The resultant implant was flexible, had lubricious surfaces and could be applied over the mandrel to simulate placement over a femoral head.

Example 7

A mandrel was produced from stainless steel to the design shown in FIG. 11 with a 30 mm diameter head. The size was selected so as to be suitable for use in a sheep pre-clinical model. Blends of Tecophilic SP-80A-150 (80 Shore A hardness and 150% equilibrium water content) and Tecophilic SP-60D-60 (60 Shore D hardness and 60% equilibrium water content), supplied by Lubrizol, were made in 5 100 ml beakers with the following compositions:
  a. Beaker 1—100% SP-80A-150
  b. Beaker 2—75% SP-80A-150: 25% SP-60D-60
  c. Beaker 3—50% SP-80A-150: 50% SP-60D-60
  d. Beaker 4—25% SP-80A-150: 75% SP-60D-60
  e. Beaker 5—100% SP-60D-60

The mandrel was slowly dipped into Beaker 1 and removed. This step was repeated three times. The mandrel was then inverted to stop drip formation and left to dry for 1 minute. The mandrel was then dipped into Beaker 2 three times and similarly removed and inverted. The sequential dipping continued through to Tank 5, after which the mandrel was dipped into Tank 4, Tank 3, Tank 2 and finally Tank 1. The coated mandrel was then placed in a vacuum oven to dry overnight with an air flow of 0.5 L/min. The implant could then be removed from the mandrel. The application of the coatings to incompletely dried prior coatings meant that there were no distinct boundaries between the layers. The implant was trimmed and weighed both dry and after fully hydrating. The water capacity was 45%.

While these examples have been demonstrated using dip coating, one skilled in the art would recognize that the same polymer combination could be readily used in an electrospinning manufacture either as a bi-component fiber or two separate fibers.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. Apparatus for treating osteoarthritis in a joint having a bone with a convex end, the apparatus comprising:

an elastomeric cap comprising:
  a balloon-shaped region sized to fit over the convex end of the bone; and
  a collar-shaped region extending from the balloon-shaped region, the collar-shaped region having a diameter that is smaller than the maximum diameter of the balloon-shaped region;
wherein the elastomeric cap is configured to be retained on the convex end of the bone by means of the collar-shaped region;
wherein the elastomeric cap further comprises a body having an outer layer configured to face away from the bone, an inner layer configured to face towards the bone and a center layer located between the outer and inner layers;
wherein the layers comprise boundaries between adjacent layers and are merged at the boundaries so that there is not a distinct interface between adjacent layers;
wherein each layer comprises at least one of a first polymer having water content and elastic properties and a second polymer having strength and wear resistance properties;
wherein each layer comprises a blend of the first polymer and the second polymer;
wherein the outer and inner layers comprise a majority of the first polymer and the center layer comprises a majority of the second polymer; and
wherein the body further comprises additional layers between the center layer and the outer and inner layers, and the ratio of the first polymer to the second polymer in each of the additional layers is progressively decreased from the outer and inner layers to the center layer.

2. Apparatus according to claim 1 wherein the first polymer is a hydrogel polymer.

3. Apparatus for treating osteoarthritis in a joint having a bone with a convex end, the apparatus comprising:
an elastomeric cap comprising:
  a balloon-shaped region sized to fit over the convex end of the bone; and
  a collar-shaped region extending from the balloon-shaped region, the collar-shaped region having a diameter that is smaller than the maximum diameter of the balloon-shaped region;
wherein the elastomeric cap is configured to be retained on the convex end of the bone by means of the collar-shaped region;
wherein the elastomeric cap further comprises a body having an outer layer configured to face away from the bone, an inner layer configured to face towards the bone and a center layer located between the outer and inner layers;
wherein the layers comprise boundaries between adjacent layers and are merged at the boundaries so that there is not a distinct interface between adjacent layers;
wherein each layer comprises at least one of a first polymer having water content and elastic properties and a second polymer having strength and wear resistance properties;
wherein each layer comprises a blend of the first polymer and the second polymer;
wherein the outer and inner layers comprise a majority of the first polymer and the center layer comprises a majority of the second polymer; and
wherein the ratio of the at least first and second polymers in the outer layer differs from the ratio of the at least first and second polymers in the inner layer.

4. Apparatus according to claim 1 wherein the cap further comprises a reinforcing member disposed in the center layer.

5. Apparatus according to claim 4 wherein a portion of the reinforcing member extends beyond the distal end of the collar-shaped region.

6. Apparatus according to claim 1 further comprising an insertion tool, the insertion tool comprising:
a handle; and
at least two prongs extending from the handle, wherein each of the at least two prongs has a clip attached to the distal end of each of the at least two prongs for selective attachment to the distal end of the collar-shaped region.

7. Apparatus according to claim 1 wherein the elastomeric cap is hydrated with a hydrating solution.

8. Apparatus according to claim 1 wherein the layers are made by one of dip coating, spray coating or electrospinning a mandrel.

9. A method for treating osteoarthritis in a joint having a bone with a convex end, the method comprising:
providing apparatus for treating osteoarthritis, the apparatus comprising:
  an elastomeric cap comprising:
    a balloon-shaped region sized to fit over the convex end of the bone; and
    a collar-shaped region extending from the balloon-shaped region, the collar-shaped region having a diameter that is smaller than the maximum diameter of the balloon-shaped region;
  wherein the elastomeric cap is configured to be retained on the convex end of the bone by means of the collar-shaped region;
  wherein the elastomeric cap further comprises a body having an outer layer configured to face away from the bone, an inner layer configured to face towards the bone and a center layer located between the outer and inner layers;
  wherein the layers comprise boundaries between adjacent layers and are merged at the boundaries so that there is not a distinct interface between adjacent layers;
  wherein each layer comprises at least one of a first polymer having water content and elastic properties and a second polymer having strength and wear resistance properties;
  wherein each layer comprises a blend of the first polymer and the second polymer;
  wherein the outer and inner layers comprise a majority of the first polymer and the center layer comprises a majority of the second polymer; and
  wherein the body further comprises additional layers between the center layer and the outer and inner layers, and the ratio of the first polymer to the second polymer in each of the additional layers is progressively decreased from the outer and inner layers to the center layer;
accessing the joint;
dislocating the joint;
fitting the elastomeric cap over the convex end of the bone; and
reducing the joint.

10. A method according to claim 9 wherein the joint is a hip joint and the convex end of the bone is the head of a femur.

11. A method according to claim 9 wherein the elastomeric cap is hydrated with a hydrating solution.

12. A method according to claim 9 wherein the first polymer is a hydrogel polymer.

13. A method according to claim 9 wherein the cap further comprises a reinforcing member disposed in the center layer.

14. A method according to claim 13 wherein a portion of the reinforcing member extends beyond the distal end of the collar-shaped region.

15. A method according to claim 9 wherein the apparatus further comprises an insertion tool, the insertion tool comprising:
 a handle; and
 at least two prongs extending from the handle, wherein each of the at least two prongs has a clip attached to the distal end of each of the at least two prongs for selective attachment to the distal end of the collar-shaped region.

16. A method according to claim 9 wherein the layers are made by one of dip coating, spray coating or electrospinning a mandrel.

17. A method for treating osteoarthritis in a joint having a bone with a convex end, the method comprising:
 providing apparatus for treating osteoarthritis, the apparatus comprising:
  an elastomeric cap comprising:
   a balloon-shaped region sized to fit over the convex end of the bone; and
   a collar-shaped region extending from the balloon-shaped region, the collar-shaped region having a diameter that is smaller than the maximum diameter of the balloon-shaped region;
  wherein the elastomeric cap is configured to be retained on the convex end of the bone by means of the collar-shaped region;
  wherein the elastomeric cap further comprises a body having an outer layer configured to face away from the bone, an inner layer configured to face towards the bone and a center layer located between the outer and inner layers;
  wherein the layers comprise boundaries between adjacent layers and are merged at the boundaries so that there is not a distinct interface between adjacent layers;
  wherein each layer comprises at least one of a first polymer having water content and elastic properties and a second polymer having strength and wear resistance properties;
  wherein each layer comprises a blend of the first polymer and the second polymer;
  wherein the outer and inner layers comprise a majority of the first polymer and the center layer comprises a majority of the second polymer; and
  wherein the ratio of the at least first and second polymers in the outer layer differs from the ratio of the at least first and second polymers in the inner layer;
 accessing the joint;
 dislocating the joint;
 fitting the elastomeric cap over the convex end of the bone; and
 reducing the joint.

* * * * *